United States Patent [19]

Lee et al.

[11] Patent Number: 4,806,702
[45] Date of Patent: Feb. 21, 1989

[54] PROCESS FOR THE PREPARATION OF THE PARYLENE DIMER

[75] Inventors: Chinsoo Lee; David R. Bassett, both of Charleston, W. Va.

[73] Assignee: Union Carbide Corporation, Danbury, Conn.

[21] Appl. No.: 53,732

[22] Filed: May 26, 1987

[51] Int. Cl.$^4$ .................................................. C07C 2/72
[52] U.S. Cl. .................................... 585/429; 585/428; 585/469
[58] Field of Search ................ 585/426, 428, 429, 469

[56] References Cited

U.S. PATENT DOCUMENTS 4,532,369  7/1985  Härtner ............................. 585/469
4,675,462  6/1987  Ungarelli et al. ................... 585/426

FOREIGN PATENT DOCUMENTS 183083  4/1986  European Pat. Off. .

OTHER PUBLICATIONS

Hawley, G. G., *The Condensed Chemical Dictionary*, Van Nostrand Reinhold and Company, © 1977, pp. 295, 419.

Primary Examiner—Patrick P. Garvin
Assistant Examiner—George R. Fourson
Attorney, Agent, or Firm—Jean B. Mauro

[57] ABSTRACT

An improved process is provided for the preparation of the dimer, 2,2-paracyclophane, which is useful as the starting material for parylene conformal coatings used in the electronics industry for the protection of various sensitive electronic components.

The process comprises optimization of the normally low yield of dimer formed by the Hofmann elimination reaction of p-methylbenzyltrimethylammonium halide by conducting the elimination reaction in the presence of dimethylsulfoxide and certain reaction promoters.

14 Claims, 2 Drawing Sheets

PROCESS FOR THE PREPARATION OF THE PARYLENE DIMER

FIELD OF THE INVENTION

This invention relates in general to an improved process for the preparaton of the parylene dimer, 2,2-paracyclophane. In one aspect, this invention is directed to an improved process for the preparation of 2,2-paracyclophane in relatively high yields. In a further aspect, this invention relates to a process for the preparation of the parylene dimer by the Hofmann elimination of p-methylbenzyltrimethylammonium hydroxide in the presence of dimethylsulfoxide (DMSO) and certain reaction promoters.

BACKGROUND OF THE INVENTION

Parylene is a generic term applied to a class of poly-p-xylylenes which are derived from a dimer of the structure:

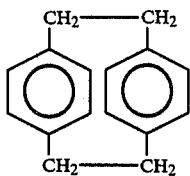

Parylene is an inert, transparent, conformal coating which has excellent barrier properties and can be used at relatively high temperatures. Due to its ability to provide thin films and conform to substrates of varied geometric shapes, it is ideally suited for use as a conformal coating in a wide variety of fields, particularly in the electronics industry.

However, the dimer itself, from which the parylene coating is prepared, is made via the pyrolysis of p-xylene or Hofmann elimination reaction of p-methylbenzyltrimethylammonium hydroxide, and is usually obtained in relatively low yields. Accordingly, the overall process for the application of parylene as a conformal coating is expensive and severely restricts its application where it might otherwise be used.

The preparation of p-xylylene polymers by various routes has been reported in the patent literature. For example, U.S. Pat. No. 2,719,131 which issued in Sept. 27, 1955 to E. I. DuPont de Nemours and Company disclosed a process for preparing poly-p-xylene wherein the vapors of p-xylene were pyrolyzed in the presence of chlorine gas.

Also in British Pat. No. 650,947 which was granted Mar. 7, 1951, polymer formation was detected on the walls of a cooling chamber after p-xylene was vaporized and pyrolyzed.

In U.S. Pat. No. 3,149,175 which issued Sept. 15, 1964 a process was reported for the preparation of di-para-xylylenes in yields of 10 percent and higher. The process involved pyrolyzing a mixture of steam and p-xylene at a temperature between about 800° C. and 1000° C. to generate a free radical and condensing the reactive diradical in a fluid medium.

More recently, U.S. Pat. No. 4,532,369 issued on July 30, 1985 to Hartmut Härtner of the Federal Republic of Germany and discloses and claims a process for the preparation of 2,2-paracyclophane from p-methylbenzyltrimethylammonium hydroxide. It is indicated in the patent that known processes which existed prior to the invention disclosed gave only low yields or the starting materials were not readily accessible. By contacting aqueous p-methylbenzyltrimethylammonium hydroxide with sodium or potassium hydroxide in the presence of dimethylsulfoxide (DMSO) the patentee indicated that yields as high as 70 percent were obtained, It was also indicated at column 1, lines 55-58, that the resulting high yields were surprising since the addition of other comparable aprotic solvents such as dimethylformamide, N-methyl-pyrollidone or sulfolane had no effect.

It is therefore an object of this invention to provide an improved process for the preparation of the dimer used in the synthesis of parylene. Another object of the invention is to provide a process for the preparation of 2,2-paracyclophane. A still further object of this invention is to provide a process for the preparation of the dimer in relative high yields as opposed to the methods disclosed in the literature to date. Another object of the invention is to provide a process which is simple and efficient and hence is effective in reducing the overall cost in the preparation of 2,2-paracyclophane and various substituted derivatives thereof. It is also an object of this invention to provide a process which is conducted in the presence of dimethylsulfoxide. A further object of this invention is to provide a process for the preparation of the dimer which provides even higher yields of the desire dimer by utilizing dimethylsulfoxide in combination with a selected class of reaction promoters. A still further object of the present invention is to provide a novel process for the preparation of the dimer, 2,2-paracyclophane more efficiently and in greater yields than heretofore. These and other objects will readily become apparant to those skilled in the art in the light of the teachings herein set forth.

SUMMARY OF THE INVENTION

In its broad aspect, the present invention is directed to an improved process for the preparation of the 2,2-paracyclophane dimer used in the preparation of parylene. The process comprises contacting an aqueous solution of p-methylbenzyltrimethylammonium hydroxide with sodium or potassium hydroxide in the presence of dimethylsulfoxide and at least one reaction promoter comprised of a crown ether or a methoxyalkoxyether.

DESCRIPTION OF THE DRAWING

A more detailed understanding of the invention will be had by reference to the drawings wherein.

Figure 1:
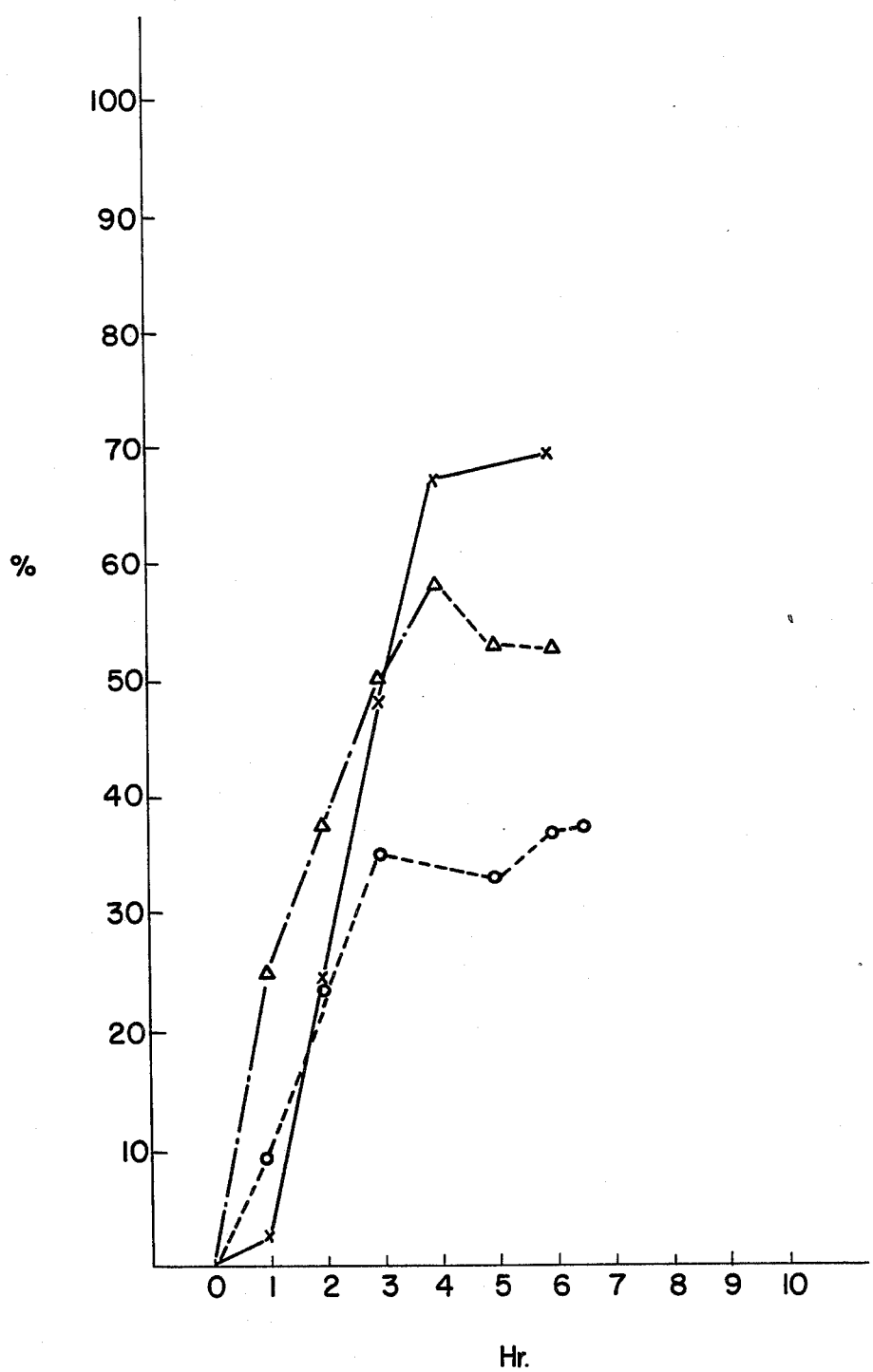
FIG. 1 is a graph showing the yield of the 2,2-paracyclophane versus time in a batch reaction according to the prior art process wherein the mole ratio of DMSO to the quaternary ammonium salt is varied.

Curve C was obtained using DMSO alone; curve B was obtained using DMSO in combination with glymes; and curve A obtained using DMSO in combination with glymes and 18 crown 6. It is evident from the drawing that higher yields of the desired dimer can be obtained in shorter periods of time when reaction promoters are employed in combination with DMSO.

DETAILED DESCRIPTION OF THE INVENTION

As indicated above, the present invention provides a simple and efficient method for the preparation of the parylene dimer in relatively high yields and from readily accessible starting materials. In contrast to the teachings of the aforementioned Härtner patent, it was unexpectedly and surprisingly found that yields of the dimer even higher than the 70 percent reported can be obtained when a reaction promoter, as herein defined, is employed in conjunction with dimethylsulfoxide.

It has been observed that while the use of dimethylsulfoxide in the Hofmann elimination reaction increased the yields of the desired dimer over those which had been disclosed in the literature, the yield could be increased even further if certain reaction promoters were also employed in the reaction system. Prior to the Härtner patent, only very small increases in yields were obtainable and hence the cost of the process remained exceedingly high and therefore the application of parylene conformal coatings was limited to the preparation of relatively expensive materials. However, even with the advent of the Härtner process, the process could still not be extended to the coating of less expensive items because of the longer reaction times needed to prepare the dimer. For the most part the use of parylene had been confined to the military or those applications in the electronics industry where the cost of the final product could justify the use of the expensive coating process.

The reaction promoters employed in the improved process of the present invention are those promoters which, when employed with dimethylsulfoxide, promote the Hofmann elimination reaction so as to shift the equilibrium of the reaction to favor the formation of the dimer as opposed to the competing reaction which favors polymer formation. The exact mechanism by which the reaction promoters operates is not readily apparant but it is believed that the presence of the promoters plays a critical part in promoting the reaction to dimer formation while retarding the reaction of the dimer so formed from polymerizing to parylene.

It has been found that a limited number of specific reaction promoters are suitable for use in the process of the present invention, and that such promoters must be used in a specific combination if increased yields of the dimer are to be obtained.

The reaction promoters which have been found to be suitable for optimizing the yield of dimer by the process of the present invention can be classified into two different categories.

The first class of compounds which can be employed as reaction promoters in the process of the present invention are the crown ethers. There are the cyclic ethers composed of carbon, oxygen and hydrogen. In practice, crown ethers containing from 4 to 6 oxygen atoms and from 12 to 18 carbon atoms can be employed in the process of the present invention. Particularly preferred is 18 crown 6.

Illustrative crown ethers which are suitable for use in the process of this invention are ethers such as 12 Crown 4 (1,4,7,10-tetraoxacyclododecane), 15 Crown 5 (1,4,7,10,13-pentaoxacyclopentadecane), 18 Crown 6 (1,4,7,10,13,16-hexaoxacyclooctadecane), benzo-15 Crown 5, bis(benzo 15 Crown 5)methyl]pimelate, bis[(12 Crown 4) 2-ylmethyl]2-dodecyl-2methyl malonate, dibenzo 18 Crown 6, dibenzo 24 Crown 6, dicyclohexano 18 Crown 6, dicyclohexano 18 Crown 6, and dicyclohexano 24 Crown 8 and the like.

The second class of reaction promoters suitable for use in the present process, are the alkoxy alkyl and the polyalkyleneoxy alkyl ethers. These compounds are sometimes referred to as "glymes" particularly when the ether is capped with a methoxy group, and include the diglymes and the tetraglymes.

Illustrative compounds within this class include amoung others, the methyl methoxyethyl ethers of the formula:

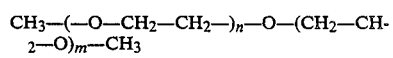

$$CH_3-(-O-CH_2-CH_2-)_n-O-(CH_2-CH_2-O)_m-CH_3$$

wherein n has a value of from 1 to 18, and more preferably from 2 to 4, and m is 0 or 1 to 4.

In practice, the process of the present invention is conducted under conditions suitable for the Hofmann elimination reaction to proceed and wherein the formation of the dimer is favored over the formation of the polymerized product, i.e., parylene. It has been found that best results are obtained when the reaction is conducted in a two phase system comprised of water and an organic phase. The starting material, i.e., the p-methylbenzyltrimethylammonium hydroxide is preferentially soluble in the aqueous phase whereas the dimer is preferentially soluble in the organic phase. Any undesirable polymer formation usually occurs at the boundary between the two phases. Thus, there is always the undesirable competing reaction for polymer formation.

The reaction as indicated is conducted in an aqueous phase and an organic phase. The organic phase is one in which the dimer is soluble and which the starting p-methylbenzyltrimethylammonium hydroxide is largely insoluble. A wide variety of organic materials can be employed as the organic medium and include such compounds as benzene, toluene, the xylenes, such as para-xylene, orthoxylene, meta-xylene, hexane, octane, methylene chloride and the like.

It was noted that in order to achieve optimum yields of the desired dimer on a consistent basis, the mole ratio of the components in the reaction mixture should be within certain specific ranges as indicated below:

(a) the mole ratio of alkaline hydroxide to the quaternary ammonium salt should be within the range of from about 2:1 to about 20:1, and preferably from about 2:1 to about 12:1.

(b) the mole ratio of dimethylsulfoxide to the quaternary ammonium salt should be within the range of from about 2:1 to about 30:1, and preferably from about 8:1 to about 20:1.

(c) the mole ratio of water to the quaternary ammonium salt should be within the range of from about 20:1 to about 70:1 and preferably from about 40:1 to about 50:1.

(d) the mole ratio of organic solvent to the quaternary salt is not necessarily critical, but good results are obtained when the mole ratio of solvent to the quaternary salt is within the range of from about 10:1 to about 80:1 and more preferably from about 20:1 to about 60:1.

(e) the mole ratio of the total reaction promoters to the quaternary salt should be within the range of from about 20:1 to about 1:1. In practice it has been observed that when the reaction promoter is a glyme it should be present within the range of from about 4:1 to about 8:1. The mole ratio of the 18 crown 6 to the quarternary salt should be within the range of from about 3:1 to about 1:1.

As indicated previously, it was unexpectedly and surprisingly found that by employing reaction promoters in conjunction with the dimethylsulfoxide, markedly increased yields of the dimer can be obtained while polymer formation is minimized.

Figure 2:
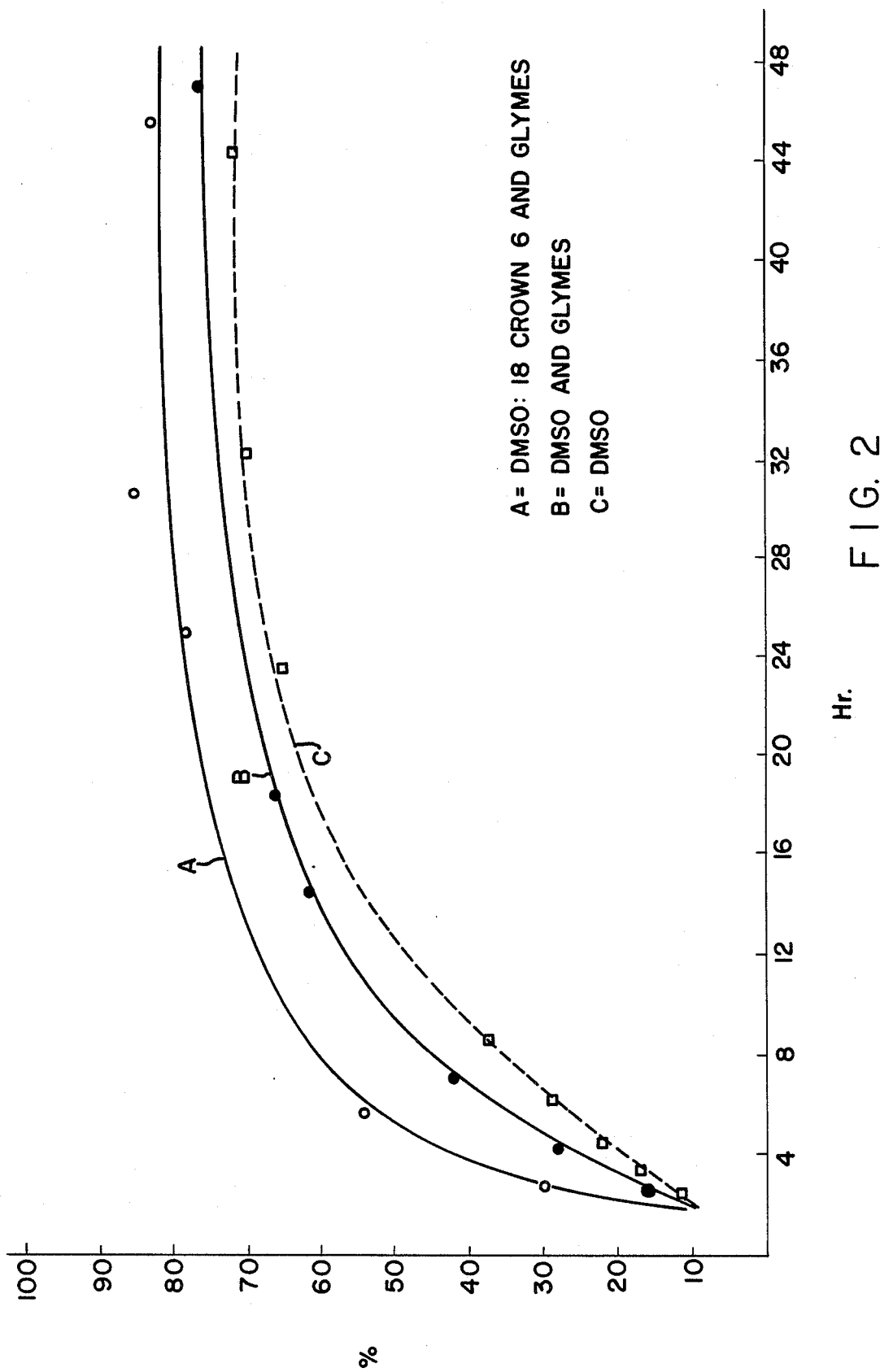
FIG. 2 is a graph which depicts the weight percent of dimer obtained by employing dimethylsulfoxide alone and in combination with certain specific reaction promoters of the present invention.

In order to obtain optimum yields of the desired dimer, the choice of reaction promoters employed is important. It has been observed that at least one of the promoters used in combination with DMSO must be a glyme to provide the highest yields in the shortest reaction period. As indicated in FIG. 2, curve B which is a combination of DMSO and a glyme provides greater yields than DMSO alone. When another reaction promoter is added to the combination,, such as a crown ether, as in curve A, maximum yields were obtained.

In practice, it has been observed that the concentration of the dimethylsulfoxide is important and not the feed configuration. Thus, in contrast to the prior art, all of the components in the present invention can be added together at one time and none need to be added dropwise. This can be a great saving in time over the process disclosed in the Harter patent. It is also quite evident from FIG. 1 that the mole ratio of the DMSO to quarternary salt is important if optimum yields are to be obtained. Additionally, it has been noted that DMSO in the presence of water and caustic can decompose at high temperatures and hence it is preferred to employ lesser amounts of DMSO when the reaction promoters of the present invention are used.

In actual practice of the process of the present invention, the mixture is stirred to insure intimate mixing of the oganic and aqueous phases. Thereafter the phases are separated and the dimer recovered from the organic phase and purified according to known techniques.

As indicated above, the process of the present invention is preferably conducted at a temperature between about 50° and about 130° C., and more preferably between about 90° and about 120° C. Temperatures above and below this range can be employed but are less preferred.

Pressure is not critical and the reaction can be conducted at atmospheric, subatmospheric or super atmospheric pressures.

The p-methylbenzyltrimethylammonium hydroxide is a well known compound and has been reported in the literature. If desired, it can be prepared in situ by reaction of a base on the corresponding quarternary ammonium salt such as the halide.

As also indicated, the prior art process provided relatively low yields of the desired dimer, largely due to the existence of competing reactions which resulted in relatively large amounts of polymer formation. Hence, until the Härtner process as described in the aforementioned U.S. Pat. No. 4,532,369, attempts to increase the yield of the dimer were for the most part failures, or at most, only small incremental increases in yields were obtained.

Due to the difficulties in finding an acceptable process for preparing the dimer, to date, it has been possible to achieve only minor increases in yield of the desired dimer. In many instances when high yields have been indicated in the literature, it has not been possible to reproduce them with the degree of consistency necessary for an efficient commercial operation. Moreover, as indicated above, DMSO is known to decompose at high temperatures, and thus attempts to increase yields of the dimer by increasing the concentration of DMSO were found to be unsatisfactory.

As indicated above, parylene is an excellent, inert, transparent conformal coating which, due to its unusual properties, renders it particularly suitable for a wide variety of applications particularly in the electronics industry. Methods of applying the coatings starting from the dimer, and equipment for effecting such applications are all well known and readily available.

The following examples illustrate the best mode presently contemplated for the practice of this invention.

EXAMPLE 1

PREPARATION OF PARACYCLOPHANE USING DMSO

A mixture of 509.2 gram of p-xylene, 20.3 gram of KOH in 20.3 ml of water, 12.35 gram of p-methylbenzyltrimethylammmonium chloride in 8.95 ml of water, and 50.4 gram of DMSO is charged to a one liter glass reactor equipped with stirrer and condenser. Nitrogen is swept slowly through the system. The solution is heated to 90° C. over a period of one hour. Stirring is continued for 40–50 hours at 90°–91° C., throughout the reaction. Reactor samples are taken, and measured for the 2,2-paracyclophane concentrations in the reactor by (G.C.) vapor-phase chromatographic analysis. Product yields are also calculated based on the G.C. analysis. The results obtained are shown in Table I below:

TABLE I

| PARACYCLOPHANE CONCENTRATION DURING REACTION | | | | | | | | |
|---|---|---|---|---|---|---|---|---|
| Sample: | 1 | 2 | 3 | 4 | 5 | 6 | 7 | 8 |
| Time (hrs): | 0 | 2.5 | 4.25 | 6.0 | 8.5 | 24.25 | 32.25 | 44.0 |
| Yield (%): | 0 | 11.4 | 22.7 | 29.1 | 38.1 | 63.4 | 70.8 | 72.1 |

EXAMPLE 2

PREPARATION OF PARACYCLOPHANE WITH DMSO AND GLYMES

The process of Example 1 is repeated except that a mixture of 402.3 gram of p-xylene, 20.3 gram of KOH in 20.3 ml of water. 12.35 gram of p-methylbenzyltrimethylammonium chloride in 8.95 ml of water, 50.4 gram of DMSO, 51.8 gram of tetraglyme and 50.1 gram of diglyme is used. The yields are obtained by measuring the 2,2-paracyclophane content of residues by G.C. analysis. The results obtained are shown in Table II below:

TABLE II

| PARACYCLOPHANE CONCENTRATION DURING REACTION | | | | | | | | | |
|---|---|---|---|---|---|---|---|---|---|
| Sample: | 1 | 2 | 3 | 4 | 5 | 6 | 7 | 8 | 9 |
| Time (hrs) | 0 | 1.0 | 2.25 | 4.0 | 6.75 | 10.25 | 14.0 | 17.75 | 47 |
| Yield (%) | 0 | 11.4 | 22.7 | 29.1 | 38.1 | 63.4 | 70.8 | 72.1 | 77 |

EXAMPLE 3

PREPARATION OF PARACYCLOPHANE WITH DMSO, GLYMES AND CROWN ETHER

The process of Example 2 is repeated except that 10.1 gram of 18 crown 6 is added to the reaction mixture. The yields are obtained by measureing the 2,2-paracyclophane content of residues by G.C. analysis. The results are shown in Table III below:

TABLE III

| | PARACYCLOPHANE CONCENTRATION DURING REACTION | | | | | | | |
|---|---|---|---|---|---|---|---|---|
| Sample: | 1 | 2 | 3 | 4 | 5 | 6 | 7 | 8 |
| Time (hrs): | 0 | 2.0 | 2.66 | 5.0 | 20 | 24 | 29 | 45.0 |
| Yield (%): | 0 | 20 | 30 | 54.7 | 75.4 | 78.9 | 83.5 | 84.2 |

EXAMPLE 4
PREPARATION OF PARACYCLOPHANE USING DMSO

A mixture of 457.7 grams of p-xylene, 32.32 grams of NaOH in 48.48 ml of water, 29.0 grams of p-methylbenzyltrimethylammonium chloride in 18.1 ml of water and 118.5 grams of DMSO is charged in a one liter stainless steel reactor equipped with stirrer. Nitrogen is used to regulate reaction pressure at 35 psi. the solution is heated to 120 degrees C. over a period of 1 hour. Stirring is continued for 10-19 hours at 120-121 degrees C. throughout the reaction study. The reactor samples are taken and measured for the 2,2-paracyclophane concentration in the reactor by (G.C.) vapor-phase chromatographic analysis. The results are shown in table IV below:

TABLE IV

| | PARACYCLOPHANE CONCENTRATION DURING REACTION | | | | | |
|---|---|---|---|---|---|---|
| Sample: | 1 | 2 | 3 | 4 | 5 | 6 |
| Time (hrs); | 0 | 1 | 2 | 3 | 4 | 5 |
| Yield (%): | 0 | 2.5 | 25 | 47.5 | 67.5 | 70 |

EXAMPLE 5
PREPARATION OF PARACYCLOPHANE USING DMSO

A mixture of 539 grams of p-xylene, 33.6 grams of NaOH in 50.4 ml of water, 24.9 grams of p-methylbenzyltrimethylammonium chloride in 18.01 ml of water and 21.7 grams of DMSO is charged in a one liter stainless steel reactor equipped with stirrer. Nitrogen is used to regulate reaction pressure at 35 psi. the solution is heated to 120 degrees C. over a period of 1 hour. Stirring is continued for 10-19 hours at 120-121 degrees C. throughout the reaction study. The reactor samples are taken and measured for the 2,2-paracyclophane concentration in the reactor by (G.C.) vapor-phase chromatographic analysis. The results are shown in table V below:

TABLE V

| | PARACYCLOPHANE CONCENTRATION DURING REACTION | | | | | | |
|---|---|---|---|---|---|---|---|
| Sample: | 1 | 2 | 3 | 4 | 5 | 6 | 7 |
| Time (hrs); | 0 | 1 | 2 | 3 | 5 | 6 | 6.5 |
| Yield (%): | 0 | 9 | 23 | 35 | 32.5 | 37 | 37.5 |

EXAMPLE 6
PREPARATION OF PARACYCLOPHANE USING DMSO

A mixture of 490.2 grams of p-xylene, 32.8 grams of NaOH in 49.2 ml of water, 24.94 grams of p-methylbenzyltrimethylammonium chloride in 18.06 ml of water and 64.8 grams of DMSO is charged in a one liter stainless steel reactor equipped with stirrer. Nitrogen is used to regulate reaction pressure at 35 psi. the solution is heated to 120 degrees C. over a period of 1 hour. Stirring is continued for 10-19 hours at 120-121 degrees C. throughout the reaction study. The reactor samples are taken and measured for the 2,2-paracyclophane concentration in the reactor by (G.C.) vapor-phase chromatographic analysis. The results are shown in table VI below:

TABLE VI

| | PARACYCLOPHANE CONCENTRATION DURING REACTION | | | | | | |
|---|---|---|---|---|---|---|---|
| Sample: | 1 | 2 | 3 | 4 | 5 | 6 | 7 |
| Time (hrs); | 0 | 1 | 2 | 3 | 4 | 5 | 6 |
| Yield (%): | 0 | 25 | 37.5 | 50 | 58 | 52.5 | 52.5 |

Although the invention has been illustrated by the preceding examples, it is not to be construed as being limited to the materials employed therein, but rather the invention is directed to the generic area as hereinbefore disclosed. Various modifications and embodiments thereof may be made without departing from the spirit or scope thereof.

What is claimed is:

1. An improved process for the preparation of the 2,2-paracyclophane dimer used in the preparation of parylene, which comprises contacting an aqueous solution of p-methylbenzyltrimethylammonium halide with an alkaline hydroxide in the presence of dimethylsulfoxide and at least one reaction promoter selected from the group consisting of:

(a) a methyl alkyleheoxy ether of the formula:

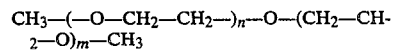

wherein n has a value of from 1 to 18, and and m is 0 or 1 to 4, and (b) a crown ether having from 4 to 6 oxygen atoms and from 12 to 18 carbon atoms, and
thereafter recovering said 2,2-paracyclophane.

2. The process of claim 1 wherein the process is effected in the presence of an inert water-immiscible organic solvent.

3. The process of claim 2 wherein said solvent is selected from the group of benzene, toluene, paraxylene, ortho-xylene, meta-xylene, hexane, octane, and methylene chloride.

4. The process of claim 1 wherein said crown ether is 1,4,7,10,13,16-hexaoxacyclooctadecane.

5. The process of claim 1 wherein said methyl alkyleneoxy ether is diglyme.

6. The process of claim 1 wherein said methyl alkyleneoxy ether is tetraglyme.

7. The process of claim 1 wherein said alkaline hydroxide is sodium hydroxide.

8. The process of claim 1 wherein said alkaline hydroxide is potassium hydroxide.

9. An improved process for the preparation of 2,2-paracyclophane which comprises contacting an aqueous solution of p-methylbenzyltrimethylammonium chloride with an alkaline hydroxide in the presence of an inert, water-immiscible organic solvent, dimethylsulfoxide, and a compound selected from the group consisting of:

(a) methyl methoxyethyl ether of the formula

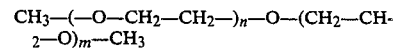

wherein n has a value of from 1 to 18, and m is 0 or 1 to 4, (b) 1,4,7,10,13,16-hexaoxacyclooctadecane, and (c) mixtures thereof and thereafter recovering said 2,2-paracyclophane.

10. The process of claim 9 wherein said alkaline hydroxide is sodium hydroxide.

11. The process of claim 9 wherein said alkaline hydroxide is potassium hydroxide.

12. The process of claim 9 wherein said organic solvent is xylene.

13. The process of claim 9 wherein said methyl methoxyethyl ether is diglyme.

14. The process of claim 9 wherein said methyl methoxethyl ether is tetraglyme.

* * * * *